June 20, 1972 W. H. JESSEL, JR., ET AL Plant Pat. 3,216
CHRYSANTHEMUM PLANT
Filed Oct. 14, 1970
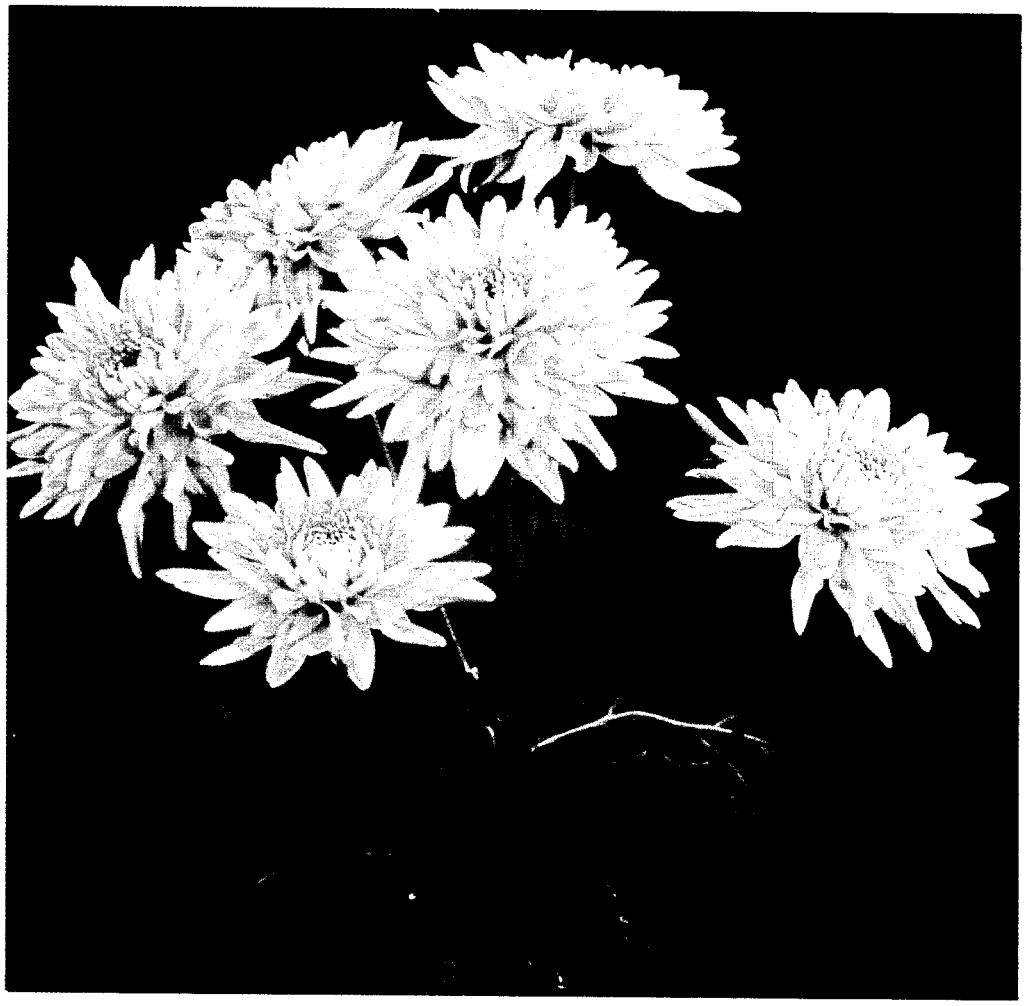
INVENTORS
WALTER H. JESSEL, JR.,
WILLIAM E. DUFFETT
BY
Oberlin, Maky, Donnelly & Renner
ATTORNEYS

United States Patent Office

Plant Pat. 3,216
Patented June 20, 1972

3,216

CHRYSANTHEMUM PLANT

Walter H. Jessel, Jr., Doylestown, and William E. Duffett, Akron, Ohio, assignors to Yoder Brothers, Inc., Barberton, Ohio

Filed Oct. 14, 1970, Ser. No. 80,824
Int. Cl. A01h *5/00*
U.S. Cl. Plt.—79 1 Claim

The present invention comprises a new and distinct cultivar of chrysanthemum plant which is a sport of the unpatented but commercially well-known cultivar known in the United States as Stingray.

The new cultivar is similar in many respects to Stingray, having the same characteristics of:

(1) Flower size.
(2) Flower form.
(3) Foliage size.
(4) Foliage shape.
(5) Foliage color.
(6) Plant vigor.

The new cultivar is distinguished from Stingray by the following characteristics:

(1) A lighter orange bronze color.
(2) Two to three days earlier response.
(3) More uniform response within a flowering block.

The new cultivar was selected from a flowering block of the parent variety in Barberton, Ohio, and when asexually reproduced by cuttings has been found to retain its distinctive characteristics through successive propagations.

The new cultivar when grown in the vicinity of Barberton, Ohio, has a response period of approximately 10 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern, mid-western United States and California is from January through December. In Florida, from December through April, and in the southern United States from November through April.

The accompanying drawing shows the unique characteristics of the new cultivar, the color being as nearly true as possible with color illustrations of this type.

In the description which follows, color references are to the Munsell Color Book, 1963 edition, and comparisons in color have been made with the cultivar Stingray. It should be noted that some difficulty was encountered in matching the colors, with the values indicated being the closest available color key.

Botanical classification: *Chrysanthemum morifolium.*

Bloom:

*Size.*—3¼".
*Fully expanded.*—3¾".
*Borne.*—Clusters on elongated pedicels.
*Stems.*—Wiry.
*Form.*—Decorative.
*Permanence.*—7–10 days.

| | Copperay | Stingray |
|---|---|---|
| Color: | | |
| Center of flower | Red bronze, 5YR5/10 to orange bronze, 7.5YR7/10. | Yellow bronze, 2.5Y7/8 to light yellow bronze, 2.5Y7/6. |
| Base of petals | Orange bronze, 5YR6/10 to yellow bronze, 10YR7/12. | Red bronze, 10R3/10 to orange bronze, 1.25YR5/12. |
| Inside of petals | Orange bronze, 7.5YR6/10 to light yellow bronze, 10YR7/10. | Orange bronze, 1.25YR 5/12 to orange bronze, 2.5YR5/10. |
| Reverse of petals. | Yellow bronze, 2.5Y7/10 to light yellow bronze, 2.5Y8/8. | Yellow bronze, 10YR6/10 to yellow bronze, 2.5Y7/8. |
| Tonality from a distance. | Orange bronze | Red bronze. |
| Discoloration | Light yellow bronze, 10YR7/10. | Orange bronze, 2.5YR 5/10. |

Petals:

*Texture.*—Smooth.
*Appearance and form*—Open at base, center ridged, tapering to a sharp point.
*Arrangement.*—Composite, whorled on a single receptacle.
*Persistence.*—Resist shatter.
*Fragrance.*—Typical chrysanthemum.

Reproductive organs:

*Stamen, anthers.*—None to 25.
*Pollen.*—None to scant.
*Arrangement.*—Clustered in center of flower, if present.
*Styles.*—Present both ray and disc florets.
*Length.*—Short.
*Ovaries.*—At the base of petal attached to receptacle.

Plant:

*Form.*—Herbaceous.
*Growth.*—Upright.
*Height, depending on culture.*—46".
*Spread.*—None when grown single stem to moderate when grown pinched.

Foliage:

*Top side.*—Green, 7.5GY3/4.
*Size.*—7" long, 4¾" wide.
*Quantity.*—Numerous.
*Shape.*—Spatulate lobed.
*Texture.*—Smooth.
*Ribs and veins.*—Very prominent.
*Edge.*—Deeply indented.
*Serration.*—Slight.
*Underside.*—Light green, 7.5GY5/4.
*Stipules.*—Prominent.

We claim:

1. A new and distinct cultivar of chrysanthemum characterized particularly as to uniqueness in comparison with the parent cultivar Stingray, by its lighter, more orange-bronze color, a two to three day earlier response period, and a more uniform response within a flowering block.

No references cited.

ROBERT E. BAGWILL, Primary Examiner

Dedication

PP. 3,216.—*Walter H. Jessel, Jr.*, Doylestown, and *William E. Duffett*, Akron, Ohio. CHRYSANTHEMUM PLANT. Patent dated June 20, 1972. Dedication filed Feb. 6, 1975, by the assignee, *Yoder Brothers, Inc.* Hereby dedicates to the Public the entire remaining term of said patent.

[*Official Gazette July 1, 1975.*]